United States Patent [19]

Suzuki et al.

[11] 4,008,265
[45] Feb. 15, 1977

[54] NOVEL BISPHENOXY CARBOXYLIC ACID DERIVATIVES AND THEIR SALTS

[75] Inventors: Yoshio Suzuki, Itami; Masayoshi Minai, Minoo; Noritaka Hamma, Ibaragi; Eiichi Murayama, Takarazuka; Shunji Aono, Toyonaka, all of Japan

[73] Assignee: Sumitomo Chemical Company, Limited, Osaka, Japan

[22] Filed: July 23, 1974

[21] Appl. No.: 491,033

Related U.S. Application Data

[63] Continuation of Ser. No. 255,244, May 19, 1972, abandoned.

[52] U.S. Cl. .................. 260/473 G; 260/246 B;
260/247.2 B; 260/268 C; 260/293.8; 260/295 M; 260/303 R; 260/307 R; 260/326.47; 260/345; 260/347.3; 260/471 C; 260/471 A; 260/559; 424/328
[51] Int. Cl.$^2$ .................................. C07C 69/66
[58] Field of Search .................. 260/473 G

[56] References Cited

UNITED STATES PATENTS

| | | |
|---|---|---|
| 3,474,128 | 10/1969 | Griot .................. 260/473 G |
| 3,542,795 | 11/1970 | Griot .................. 260/473 G |
| 3,668,234 | 6/1972 | Griot .................. 260/473 G |
| 3,716,583 | 2/1973 | Nakamura et al. .................. 260/473 G |
| 3,970,694 | 7/1976 | Minai et al. .................. 260/473 G |

FOREIGN PATENTS OR APPLICATIONS

2,326,061  12/1974  Germany .................. 260/473 G

*Primary Examiner*—Paul J. Killos
*Attorney, Agent, or Firm*—Stevens, Davis, Miller & Mosher

[57] ABSTRACT

Bisphenoxy carboxylic acid derivatives useful as an antiarteriosclerosis agent with good absorbability and low toxicity, which are novel compounds represented by the general formula,

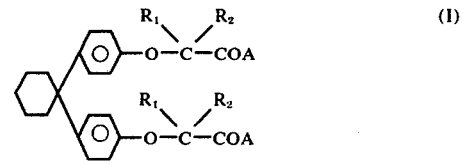

wherein $R_1$ and $R_2$ represent hydrogen atoms or lower alkyl groups and A represents

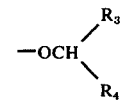

(wherein in case $R_3$ is a hydrogen atom, $R_4$ represents an amino-lower-alkyl group, an N-lower-alkylaminoalkyl group, a heterocyclic group, or a heterocyclic group-substituted alkyl group; or $R_3$ and $R_4$ may join through an intermediary hetero atom to form a heterocyclic group and if said hetero atom is a nitrogen atom, this nitrogen atom can bear a lower alkyl group as a substituent) or

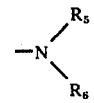

(wherein $R_5$ represents a hydrogen atom, a hydroxyalkyl group or a derivative thereof, and $R_6$ represents a hydroxyalkyl group or a heterocyclic group; or $R_5$ and $R_6$ may join to form a cyclic group, or may join through another intermediary hetero atom to form a heterocyclic group and if said hetero atom is a nitrogen atom, this nitrogen atom can bear a lower alkyl group as a substituent), are prepared by reacting a bisphenoxy acid represented by the general formula,

wherein $R_5$ and $R_6$ have the same meanings as defined above, or a salt thereof. Alternatively, the bisphenoxy carboxylic acid derivatives represented by the said general formula (I), wherein A is

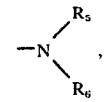

$R_5$ is hydrogen and $R_6$ is a hydroxyalkyl group, are prepared by heating a bisphenoxy acid derivative represented by the general formula,

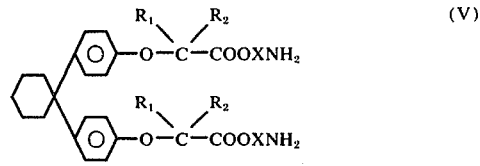

wherein $R_1$ and $R_2$ have the same meanings as defined above and X represents an alkylene chain.

5 Claims, No Drawings

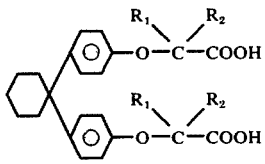

wherein $R_1$ and $R_2$ have the same meanings as defined above, or a reactive derivative thereof with a hetero atom-containing alcohol compound represented by the general formula,

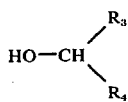

wherein $R_3$ and $R_4$ have the same meanings as defined above, an amine derivative represented by the general formula,

NOVEL BISPHENOXY CARBOXYLIC ACID DERIVATIVES AND THEIR SALTS

This is a continuation, of application Ser. No. 255,244, filed May 19, 1972, now abandoned.

This invention relates to novel anti-atherosclerosis agents. More particularly, the invention pertains to novel agents which are useful for the lowering of elevated levels of cholesterol or lipids.

Atherosclerosis is an adult disease for which there is no known satisfactory cure. Although the cause for atherosclerosis is not yet known in spite of discussions in the academic circles, it has broadly been recognized that one of the most significant histopathological manifestations of atherosclerosis is the deposition of lipids in the blood. Accordingly, research has been directed to the disturbed metabolism of lipids, and attention has been given to the extraordinarily elevated level of cholesterol in the blood.

A number of experimental and clinical facts have been reported, which indicate the relationship between atherosclerosis and elevated blood cholesterol or lipid level. Hence, the development of agents to reduce the elevated blood cholesterol or lipid level is considered extremely important for the prevention of atherosclerosis.

Concentrated effects have heretofore been made for the development of such agents for lowering cholesterol or lipids and a number of compounds have been tested clinically, but none of them have proved to be completely satisfactory. Some of them are fairly effective but produce significantly harmful side effects, and others have inadequate effectiveness, so that they are required to be administered in large doses.

A group of compounds practically employed presently for the above purpose includes ethyl α-(p-chlorophenoxy)-isobutyrate (clofibrate).

The present inventors have found a group of novel compounds which are effective as cholesterol-lowering agents and which are substantially non-toxic and less hepatomegalic than clofibrate.

An object of the present invention is to provide novel bisphenoxycarboxylic acid derivatives usable as anti-atherosclerosis agents which have prominent effects and extremely high in admissibility.

Another object of the invention is to provide an economical and industrially advantageous process for producing the above-mentioned bisphenoxycarboxylic acid derivatives.

A further object of the invention is to provide a pharmaceutical composition containing such antiatherosclerosis agent.

Other objects and merits of the invention will be apparent from the following description.

In order to accomplish these objects, the present invention provides novel bisphenoxycarboxylic acid derivatives of the formula,

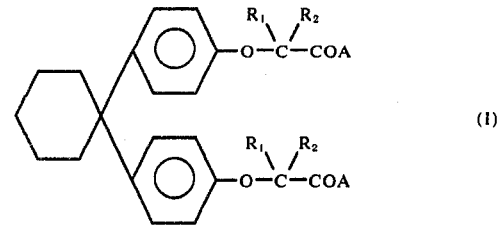

wherein $R_1$ and $R_2$ represent hydrogen atoms or lower alkyl groups and A represents

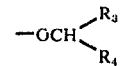

(wherein in case $R_3$ is a hydrogen atom, $R_4$ represents an amino-lower-alkyl group, an N-lower-alkylaminoalkyl group, a heterocyclic group, or a heterocyclic group-substituted alkyl group; or $R_3$ and $R_4$ may join through an intermediary hereto atom to form a heterocyclic group and if said hetero atom is a nitrogen atom, this nitrogen atom can bear a lower alkyl group as a substituent) or

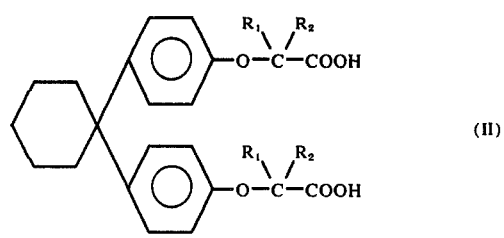

wherein $R_1$ and $R_2$ represents hydrogen atoms or lower alkyl groups, were first synthesized by the present inventors by any one of the procedures as shown by the following reaction scheme;

Procedure 1

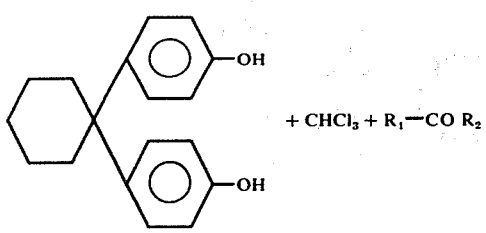

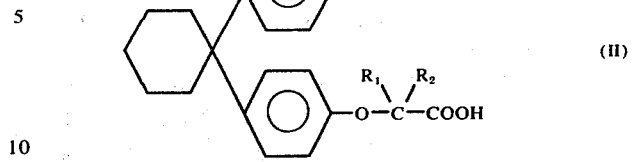

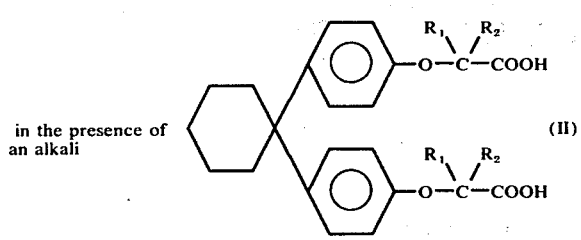

in the presence of an alkali                                                                                      (II)

Procedure 2

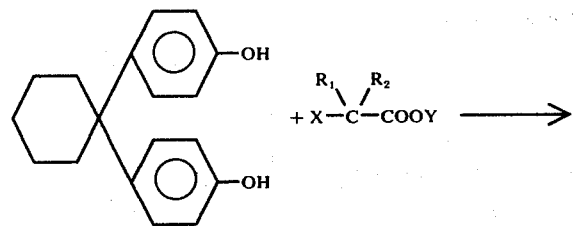

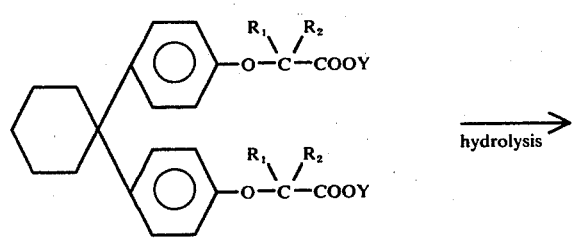

hydrolysis

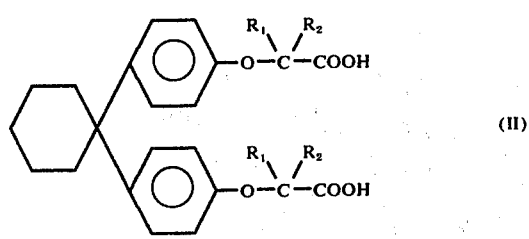

(II)

wherein $R_1$ and $R_2$ are as defined above, and Y is lower alkyl.

The phenoxy carboxylic acid derivatives of this invention may be obtained by reacting a bisphenoxy acid represented by the general formula,

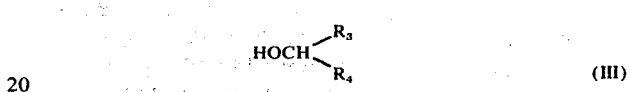

(II)

wherein $R_1$ and $R_2$ have the same meanings as defined above, or a reactive derivative thereof with a hetero atom-containing alcohol represented by the general formula,

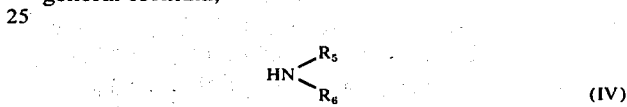

(III)

wherein $R_3$ and $R_4$ have the same meanings as defined above, or with an amine derivative represented by the general formula,

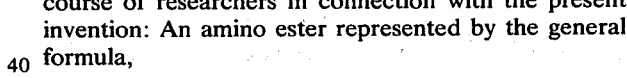

(IV)

wherein $R_5$ and $R_6$ have the same meanings as defined above, or a salt thereof.

The reaction itself in this invention can be satisfactorily carried out by the conventional procedure.

Some of the compounds of this invention can also be synthesized according to the following new reaction scheme found by the present inventors during the course of researchers in connection with the present invention: An amino ester represented by the general formula,

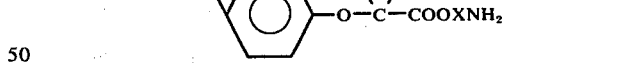

(V)

wherein $R_1$ and $R_2$ have the same meanings as defined above and X represents an alkylene chain, is heated preferably at a moderate temperature of 50° to 100° C. to form a hydroxyalkyl acid amide represented by the general formula (I), provided that A is $$-N\begin{matrix}R_5\\R_6\end{matrix},$$

$R_5$ is a hydrogen atom and $R_6$ is a hydroxyalkyl group.

The term "reactive derivative of carboxylic acid" used herein means derivatives such as a carboxylic acid halide and acid anhydride.

The term "alkylene chain" means ethylene, trimethylene or tetramethylene.

Thus, the reaction of a carboxylic acid halide of a compound represented by the general formula (II) with an alcohol represented by the general formula (III) can be satisfactorily carried out in an inert organic solvent such as, for example, benzene, toluene, ether, dioxane, tetrahydrofuran, acetone, methyl isobutyl ketone, chloroform, carbon tetrachloride or the like, or in a mixed solvent containing said organic solvent and water, in the presence or absence of an organic base such as trimethylamine, triethylamine, diethylaniline, pyridine or the like, or an inorganic base such as sodium hydroxide, potassium hydroxide, sodium carbonate, potassium carbonate, sodium hydrogen carbonate or the like.

The reaction of a carboxylic acid of the general formula (II) with a hetero atom-containing alcohol can be carried out in the above-mentioned inert solvent in the presence of a dehydration-condensation agent such as, for example, hydrochloric acid, sulfuric acid, potassium hydrogen sulfate, sodium hydrogen sulfate, toluenesulfonic acid, an ion-exchange resin, a dialkyl carbodiimide, or the like, to synthesize advantageously the objective ester.

The objective ester can also be obtained by first reacting a carboxylic acid of the formula (II) with a chloroformate ester, and then further reacting with an alcohol represented by the general formula (III), that is, by a so-called mixed-acid-anhydride method.

In the case where the hetero atom in the general formula (III) is nitrogen atom and is in a grouping of primary or secondary amine, it is desirable to protect said nitrogen atom with a benzyloxycarbonyl group, trityl group, o-nitro-phenylsulfinyl group, or the like, which can easily be split after the objective ester has been formed.

Typical examples of the hetero atom-containing alcohols for use in this invention include amino-alkyl alcohols such as ethanolamines and propanol-amines, and derivatives thereof, pyridylalkyl alcohols and derivatives thereof, pyridylalkyl alcohols and derivatives thereof, piperidyl alcohols and derivatives thereof, piperazyl alcohols and derivatives thereof, pyrrolidyl alcohols and derivatives thereof, pyrrolylalkyl alcohols and derivatives thereof, morpholyl alcohols and derivatives thereof, thiophenylalkyl alcohols, thiazonylalkyl alcohols, oxazolealkyl alcohols, furanylalkyl alcohols, and pyranyl alcohols.

The reaction of an acid halide as a reactive derivative of the bisphenoxy acid of the general formula (II) with an amine represented by the general formula (IV) can be carried out in an inert organic solvent such as benzene, toluene, a petroleum hydrocarbon, ether, dioxane, tetrahydrofuran, acetone, methyl ethyl ketone, methyl isobutyl ketone, chloroform, or carbon tetrachloride, or water, or a mixed solvent comprising water and said organic solvent, in the presence or absence of an organic base such as trimethylamine, triethylamine, diethylaniline, or pyridine, or an inorganic base such as sodium hydroxide, potassium hydroxide, sodium carbonate, potassium carbonate, or sodium hydrogen carbonate, to obtain an acid amide derivative represented by the general formula (I).

The reaction of a carboxylic acid of the general formula (II) with an amine represented by the general formula (IV) or with said amine, if necessary, after having other reactive groups protected by protecting grups can be carried out by using both reactants in equimolar amounts or either one of them in excess, in the absence or presence of a catalyst such as sulfuric acid, potassium hydrogen sulfate, toluenesulfonic acid, toluenesulfonic acid chloride, or acidic or basic ion-exchange resins, e.g. IRA-400, IR-50 or IR-120, in a solvent, if necessary, such as benzene, toluene or xylene, at 60° to 140° C. for several to several tens hours, while removing or without removing the water which is formed during the reaction. Alternatively, the objective amide compound represented by the general formula (I) can be obtained by dissolving both reactants in an inert solvent, as mentioned above in the case of the reaction between an acid halide and an amine, and reacting in the presence of a dehydrating catalyst such as a dialkyl carbodiimide at preferably −15° to 30° C. for several tens minutes to several tens hours.

The objective amide compound can also be obtained by first reacting a carboxylic acid of the general formula (II) with a reagent such as a chloroformate ester which forms a mixed-acid-anhydride at preferably −40° to 40° C., and then reacting with an amine represented by the general formula (IV) at preferably −40° to 40° C.

Further, the objective amide compound represented by the general formula (I) can be obtained by reacting an ester derivative of a carboxylic acid of the general formula (II) in which hydroxyl groups have been replaced by lower alkoxy groups, nitrophenoxy groups, nitrobenzyloxy groups, or the like, with an amine represented by the general formula (IV) in a suitable solvent such as methanol, ethanol, other alcohols, benzene, toluene, or the like, in the presence or absence of a catalyst such as sodium alcoholate, trialkylamine, potassium hydroxide, sodium hydroxide, potassium carbonate, sodium carbonate, or other inorganic bases.

Typical examples of amines represented by the general formula (IV) for use in this invention include aminoalkyl alcohols such as ethanolamine, propanolamine, diethanolamine, and derivatives thereof, heterocycloaliphatic compounds such as pyrrolidine, piperidine, piperazine, morpholine, and derivatives thereof, heterocyclic amine derivatives such as furan, thiophene, pyrrole, oxazole, thiazole, imidazole, pyrazole, pyran, pyridine, etc.

The compounds represented by the general formula (I) can be also synthesized using the catalysts of phosphine and mercaptoamine or the like from carboxylic acid represented by the formula (II) and alcohols represented by the formula (III) or amines represented by the formula (IV), by method of Oxidation-Reduction condensation disclosed in Tetrahedron Letters 1901 − 1904 (1970) or J. Am. Chem. Soc., 90, 4490 (1964).

The acid addition salts include the salt of the amine derivative (in the general formula (I), A contains amine group) with inorganic or organic acid such as hydrochloric acid, sulfuric acid, nitric acid, acetic acid, oxalic acid, tartaric acid, citric acid, malic acid, succinic acid, maleic acid, fumaric acid and the like.

The acid addition salts of the compounds which were obtained by the present invention have also good pharmaceutical properties, for instance, a high solubility and dispersibility or a favourable pH value in the solution.

The present invention further provides a pharmaceutical composition containing a bisphenoxy carboxylic acid derivative of the formula (I).

The cholesterol-lowering agents of this invention may be, for example, orally administered.

Usually the amount orally administered is 0.2 g − 1.5 g per day/human adult. The cholesterol-lowering agent may be in any suitable form which is conventional for oral administration. Thus, it may be encased in a capsule, or it may be in a liquid form, in a tablet form, or in a powder form. In preparing the agents in these various forms, the active compound may be mixed with or impregnated in a suitable solid carrier.

The process of the present invention is illustrated in more detail by the following examples, but it is not intended to limit the invention to them.

EXAMPLE 1

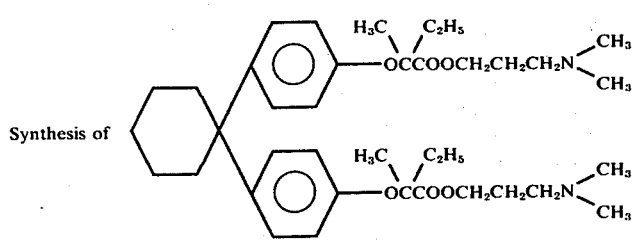

In 150 ml of anhydrous benzene, are dissolved 6 g of 1,1-bis[4′-(1″-carboxy-1″-methylpropoxy)-phenyl]-cyclohexane and 30 g of thionyl chloride, and refluxed for 2 hours with stirring. The reaction mixture is concentrated under reduced pressure to obtain a crude acid chloride. Into another solution prepared by dissolving 2.6 g of 3-dimethylaminopropanol and 2.6 g of triethylamine in 150 ml of anhydrous toluene, is added with stirring the above-obtained crude acid chloride over a period of 30 minutes at 10° C. After being stirred at the same temperature for 2 hours, the mixture is left standing overnight. The reaction mixture is washed with cold sodium carbonate, then washed with water, and further treated with activated carbon to obtain an ester. The ester thus obtained is dissolved in ether and dry hydrogen chloride gas is introduced therein to obtain a hydrochloride. The hydrochloride is thoroughly washed with ether, dehydrochlorinated with an aqueous solution of sodium carbonate, washed with water, dried and concentrated to obtain 5.0 g of the objective ester, $n_D^{25}$ 1.5212.

| Elementary analysis: | Found | Theoretical |
|---|---|---|
| C, % | 72.29 | 72.47 |
| H, % | 9.09 | 8.82 |
| N, % | 3.93 | 4.24 |

EXAMPLE 2

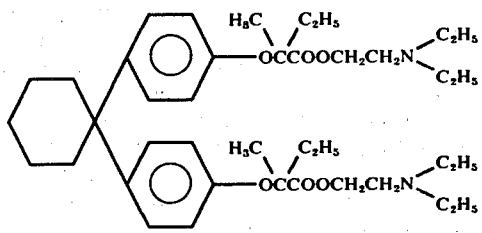

In a manner similar to that in Example 1, a crude acid chloride is obtained from 6 g of 1,1-bis[4′-(1″-carboxy-1″-methylpropoxy)-phenyl]cyclohexane, 30 g of thionyl chloride and 120 ml of anhydrous benzene. The crude acid chloride is reacted with 3 g of diethylaminoethanol and 3 g of triethylamine and treated in a manner similar to that in Example 1, to obtain 5.9 g of the objective ester, $n_D^{24}$ 1.5272.

| Elementary analysis: | Found | Theoretical |
|---|---|---|
| C, % | 72.02 | 72.03 |
| H, % | 9.45 | 9.37 |
| N, % | 4.07 | 4.20 |

EXAMPLE 3

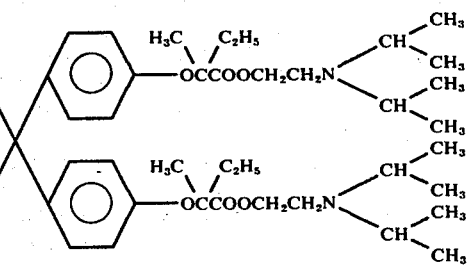

7.1 Grams of 1,1-bis[4′-(1″-carboxy-1″-methylpropoxy)-phenyl]cyclohexane and 4.9 g of 2-diisopropylaminoethanol hydrochloride are refluxed in benzene in the presence of 0.8 g of p-toluenesulfonic acid for 6 hours. Refluxing is continued while removing the formed water azeotropically with benzene. The reaction mixture is treated in a manner similar to that in Example 1 to obtain 3.1 g of the objective ester, $n_D^{25}$ 1.5195.

| Elementary analysis: | Found | Theoretical |
|---|---|---|
| C, % | 73.07 | 73.09 |
| H, % | 9.60 | 9.76 |
| N, % | 3.72 | 3.87 |

EXAMPLE 4

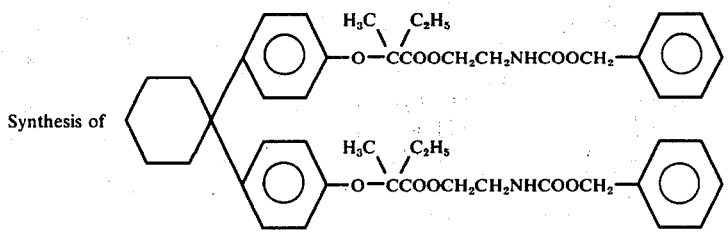

In a manner similar to that in Example 1, a crude acid chloride is obtained from 4.7 g of 1,1-bis[4'-(1''-carboxy-1''-methylpropoxy)-phenyl]cyclohexane, 30 g of thionyl chloride and 100 ml of benzene. The crude acid chloride is reacted with 3.9 g of N-benzyloxycarbonylaminoethanol and 2.3 g of triethylamine according to the procedure in Example 1. The reaction mixture is washed successively with dilute hydrochloric acid, water, an aqueous solution of sodium carbonate, and water. The washed reaction mixture is dried and treated with activated carbon. The resulting oily substance is purified by chromatography to obtain 4.0 g of the objective ester, $n_D^{22}$ 1.5501.

| Elementary analysis: | Found | Theoretical |
|---|---|---|
| C, % | 70.07 | 70.05 |
| H, % | 7.11 | 7.10 |
| N, % | 3.35 | 3.40 |

EXAMPLE 5

Synthesis of 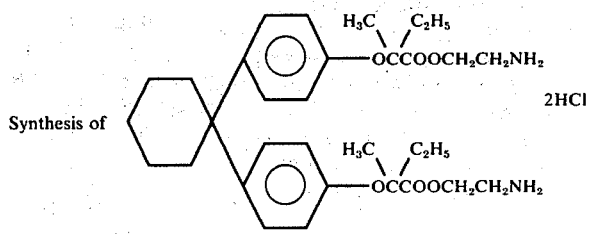

Hydrogen is introduced, at room temperature, into 150 ml of ethanol containing 1.8 g of di-N-benzyloxycarbonylaminoethanol ester of 1,1-[4'-(1''-carboxy-1''-methylpropoxy)-phenyl]cyclohexane and 0.1 g of dissolved hydrogen chloride gas, in the presence of a palladium-carbon catalyst. The reaction is complete in 2 hours, the end point being confirmed by disappearance of the spot due to the starting material in thin layer chromatography. Then, the catalyst is filtered off and the solvent is removed by distillation. The remaining oily substance is crystallized from ether to obtain 1.4 g of the objective hydrochloride, melting at 114° C. (decomp).

| Elementary analysis: | Found | Theoretical |
|---|---|---|
| C, % | 61.05 | 61.23 |
| H, % | 7.76 | 7.71 |
| N, % | 4.40 | 4.46 |
| Cl, % | 11.47 | 11.30 |

EXAMPLE 6

Synthesis of 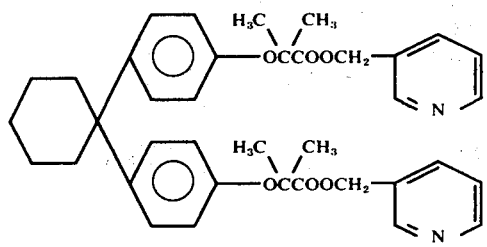

In 80 ml of dichloromethane, are dissolved 4.3 g of 1,1-bis[4'-(1''-carboxy-1''-methylethoxy)phenyl]cyclohexane and 2.2 g of triethylamine. To the resulting solution cooled below −5° C., is added dropwise with vigorous stirring 2.6 g of ethyl chloroformate over a period of 30 minutes. After being stirred at the same temperature for one hour, the mixture is admixed with a dichloromethane solution containing 3 g of pyridine carbinol while maintaining the inner temperature at −5° to 10° C. After being stirred for one hour at the same temperature and another one hour at room temperature, the reaction mixture is treated and purified as mentioned in Example 1 to obtain 3.4 g of the objective ester, $n_D^{23}$ 1.5669.

| Elementary analysis: | Found | Theoretical |
|---|---|---|
| C, % | 73.49 | 73.29 |
| H, % | 6.78 | 6.86 |
| N, % | 4.38 | 4.50 |

EXAMPLE 7

Synthesis of 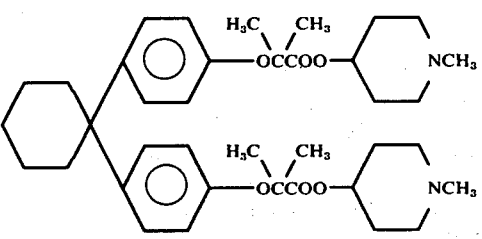

In a manner similar to that in Example 1, a crude acid chloride is obtained from 4.3 g of 1,1-bis[4'-(1''-carboxy-1''-methylethoxy)phenyl]cyclohexane, 30 g of thionyl chloride and 80 ml of anhydrous benzene. The acid chloride is reacted with 2.3 g of 4-hydroxy-N-methylpiperidine and 2.1 g of triethylamine and treated as mentioned in Example 1 to obtain 2.1 g of the objective ester, $n_D^{22}$ 1.5300.

| Elementary analysis: | Found | Theoretical |
|---|---|---|
| C, % | 71.89 | 71.89 |
| H, % | 8.55 | 8.57 |
| N, % | 4.30 | 4.41 |

EXAMPLE 8

Synthesis of 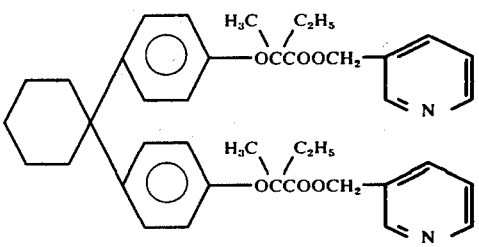

In a manner similar to that in Example 1, a crude acid chloride is obtained from 4.7 g of 1,1-bis[4'-(1''-carboxy-1''-methylpropoxy)-phenyl]cyclohexane, 30 g of thionyl chloride, and 100 ml of benzene. The acid chloride is reacted with 3 g of 3-pyridinecarbinol dissolved in 100 ml of toluene, then treated and purified as mentioned in Example 1 to obtain 5.1 g of the objective ester, $n_D^{26}$ 1.5671.

| Elementary analysis: | Found | Theoretical |
|---|---|---|
| C, % | 73.90 | 73.82 |
| H, % | 7.20 | 7.12 |
| N, % | 4.18 | 4.30 |

EXAMPLE 9

Preparation of 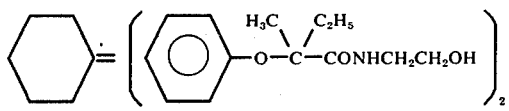

In 100 ml of dichloromethane, are dissolved 4.7 g of 1,1-bis[4'-(1''-carboxy-1''-methylpropoxy)phenyl]cyclohexane and 2.2 g of triethylamine. To the solution, is added with stirring 2.6 g of ethyl chloroformate dropwise over a period of 40 minutes at −5° C. To the mixture, after being stirred at the same temperature for 1.5 hours, is added a solution of 1.3 g of ethanolamine in 20 ml of dichloromethane dropwise over a period of 30 minutes at a temperature below −5° C. After the mixture is stirred at said temperature for one hour, the cooling bath is removed and the temperature of the mixture is brought to room temperature in 30 minutes. The mixture is stirred at room temperature for two hours, then concentrated and transferred with ether to a separatory funnel, in which the mixture is washed successively with cold dilute hydrochloric acid, water, an aqueous solution of sodium carbonate, and water. On drying and concentrating 3.4 g of the objective crude amide is obtained. On further purification by chromatography using silica gel, 2.7 g of the objective purified amide compound is obtained.

| Elementary analysis: | C | H | N |
|---|---|---|---|
| Theoretical, % | 69.28 | 8.36 | 5.05 |
| Found, % | 69.22 | 8.36 | 4.93 |

Acetyl derivative:

The above-obtained amidoalcohol is acetylated with acetyl chloride in a customary way to yield an amidoacetate compound, $n_D^{22}$ 1.5345.

| Elementary analysis: | C | H | N |
|---|---|---|---|
| Theoretical, % | 67.69 | 7.89 | 4.39 |
| Found, % | 67.62 | 7.82 | 4.40 |

EXAMPLE 10

Preparation of 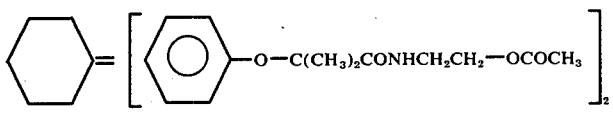

In 100 ml of anhydrous toluene, are dissolved 4.9 g of 1,1-bis[4-(1''-carboethoxy-1''-methylethoxy)phenyl]cyclohexane and 2.0 g of ethanolamine. After being admixed with 0.1 g of sodium methylate, the solution is refluxed with stirring for 20 hours.

After being cooled, the reaction mixture is washed successively with cold dilute hydrochloric acid, water, an aqueous sodium carbonate solution, and water. Then, the mixture is dried over anhydrous sodium sulfate and concentrated to yield 3.4 g of a crude amidoalcohol compound.

In 50 ml of anhydrous toluene, are dissolved 3.3 g of the above-obtained crude amidoalcohol compound and 1.4 g of triethylamine. To the solution, is added 1.1 g of acetyl chloride dropwise over a period of 20 minutes with stirring at 0° to 5° C. The mixture is stirred at said temperature for 30 minutes, then at room temperature for 3 hours, and left standing overnight. The reaction mixture is washed with cold dilute hydrochloric acid, and then with water. The mixture is dried over anhydrous sodium sulfate, concentrated, and purified by chromatography using silica gel, to yield 2.5 g of the objective amidoacetate compound, $n_D^{24}$ 1.5341.

| Elementary analysis: | C | H | N |
|---|---|---|---|
| Theoretical, % | 66.86 | 7.59 | 4.59 |
| Found, % | 66.90 | 7.61 | 4.54 |

EXAMPLE 11

Preparation of 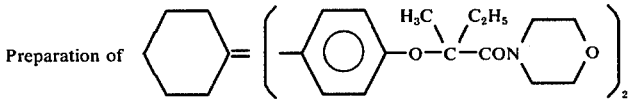

In 100 ml of toluene, are dissolved 6 g of 1,1-bis[4'-(1''-carboxy-1''-methylpropoxy)phenyl]cyclohexane and 30 g of thionyl chloride, and the solution is refluxed for 2 hours. The excess of thionyl chloride and toluene are removed by distillation under reduced pressure. Fifty milliliters of toluene is again added and removed by distillation under reduced pressure. This treatment is repeated twice more to obtain a crude acid chloride free from thionyl chloride.

To a solution of 4.5 g of morpholine and 2.7 g of triethylamine in 100 ml of anhydrous toluene, is added with stirring, at 0° to 5° C., a solution of the above-obtained crude acid chloride in 50 ml of anhydrous toluene dropwise over a period of one hour. Stirring is continued for 2 hours at the said temperature, then for another 2 hours at room temperature, and for further 2 hours at 50° C. The reaction mixture is washed successively with an aqueous dilute solution of hydrochloric acid, water, an aqueous sodium carbonate solution, and water. After removal of the solvent, the reaction product is recrystallized from benzene-petroleum ether and then from benzene-ethyl acetate to obtain 5.2 g of the objective amide compound, melting at 149° – 150° C.

| Elementary analysis: | C | H | N |
|---|---|---|---|
| Theoretical, % | 71.29 | 8.19 | 4.61 |
| Found, % | 71.25 | 8.31 | 4.62 |

EXAMPLE 12

Preparation of 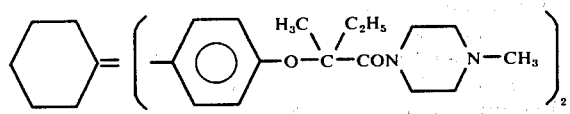

In 50 ml of toluene, are dissolved 5 g of 1,1-bis[4'-(1''-carboxy-1''-methylpropoxy)phenyl]cyclohexane, 3 g of N-methylpiperazine and 1 g of potassium hydrogen sulfate. The solution is refluxed for 30 hours in an apparatus equipped with a water-separator to effect dehydration reaction. After cooling, the reaction mixture is successively washed with cold aqueous sodium carbonate and water to obtain 4.0 g of the objective amide compound, melting at 65° to 67° C.

| Elementary analysis: | C | H | N |
|---|---|---|---|
| Theoretical, % | 72.29 | 8.18 | 8.61 |
| Found, % | 72.11 | 8.92 | 8.80 |

Hydrochloride of the objective compound, melting at 160° – 161° C. (decomp.)

EXAMPLE 13

Preparation of 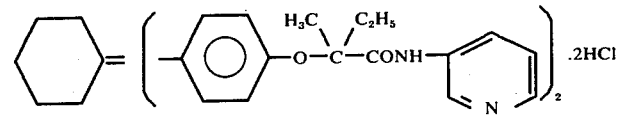

In 150 ml of toluene, are dissolved 2.2 g of 2-aminopyridine and 4 g of dicyclohexyl carbodiimide. To the solution cooled to −5° C., is added, with stirring, dropwise over a period of 10 minutes 4.5 g of 1,1-bis[-4'-(1''-carboxy-1''-methylpropoxy)phenyl]cyclohexane dissolved in 100 ml of ether and cooled to −5° C. After stirring the mixture for 20 minutes at said temperature, the cooling bath is removed and stirring is continued for further 2 hours at room temperature. After standing overnight, the reaction mixture is filtered and the filtrate is admixed with 0.2 g of acetic acid. After stirring for 30 minutes, the reaction mixture is filtered and the filtrate is washed successively with water, an aqueous sodium carbonate solution, and water. Hydrogen chloride gas is introduced into the solution and then the solution is concentrated to obtain 4.1 g of the objective amide hydrochloride, melting at 118° – 119° C.

| Elementary analysis: | C | H | N | Cl |
|---|---|---|---|---|
| Theoretical, % | 65.79 | 6.68 | 8.08 | 10.22 |
| Found, % | 65.63 | 7.04 | 7.94 | 10.13 |

EXAMPLE 14

Preparation of 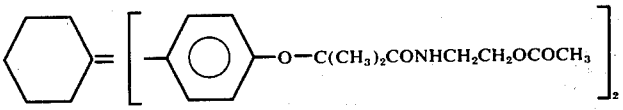

1) Preparation of 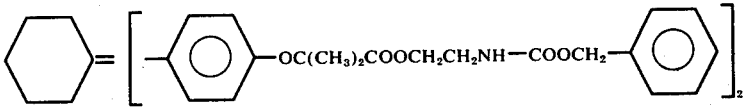

In 50 ml of benzene, are dissolved 4.6 g of 1,1-bis[4'-(1''-carboxy-1''-methylethoxy)phenyl]cyclohexane and 30 g of thionyl chloride, and the solution is refluxed for 2 hours. A crude acid chloride is obtained in a manner similar to that in Example 11. To a solution of 3.9 g of N-benzyloxycarbonylaminoethanol and 2.3 g of triethylamine in 50 ml of benzene, is added the above-obtained crude acid chloride dissolved in 50 ml of benzene dropwise over a period of one hour at 0° to 5° C. The mixture is treated in a manner similar to that in Example 11 and purified by chromatography using silica gel to obtain 4.7 g of N-benzyloxycarbonylamino ester compound, $n_D^{24}$ 1.5500.

| Elementary analysis: | C | H | N |
|---|---|---|---|
| Theoretical, % | 69.50 | 6.85 | 3.52 |
| Found, % | 69.39 | 6.90 | 3.41 |

2) Preparation of 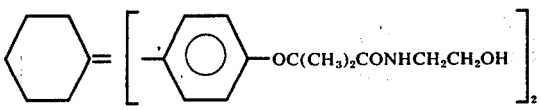

4 Grams of N-benzyloxycarbonylamino ester compound obtained in 1) is dissolved in 20 g of ethanol and admixed with 1 g of palladium-carbon. Theoretical amount of hydrogen is added to the solution at ordinary pressure in two hours. After removal of palladium-carbon by filtration, the solution is concentrated at 60° to 70° C. The concentrate is dissolved in ether and washed successively with a cold aqueous solution of hydrochloric acid, water, an aqueous sodium carbonate solution, and water. The washed solution is dried over anhydrous sodium sulfate and concentrated by heating at 60° to 70° C. to obtain 3.0 g of an amidoalcohol compound.

3. 2.0 Grams of the amidoalcohol compound and 1.0 g of dimethylaniline are dissolved in 50 ml of benzene and treated in a manner similar to that in Example 10 to obtain 1.8 g of the objective acetylamide compound, $n_D^{23}$ 1.5340.

| Elementary analysis: | C | H | N |
|---|---|---|---|
| Theoretical, % | 66.86 | 7.59 | 4.59 |
| Found, % | 66.70 | 7.62 | 4.51 |

The cholesterol lowering activity of the above-prepared compounds was tested by the following method.

Male Wistar rats weighing 130 g to 160 g were divided into several experimental groups, 5 to ten animals in each group.

Test compounds were administered orally by a stomach tube. The period of treatment was 7 days.

At the end of the test period, blood samples were collected from the inferior vena cava under light ether anesthesia and the weight of liver was recorded.

Serum cholesterol and serum triglycerides were determined.

Cholesterol lowering effect was expressed as percentage of serum cholesterol levels of control group as shown in the following Table 1. In the Table 1, compounds are referred to by number of the above-mentioned examples.

Table I

| Compound No. | Dura-Dose (mg/kg) | Seration (days) | Serum Cholesterol index[1] | liver Triglycerides index[1] | Relative weight[2] index[1] |
|---|---|---|---|---|---|
| 1 | 30 | 7 | 81 | 57 | 105 |
| 2 | 30 | 7 | 83 | 57 | 109 |
| 3 | 30 | 7 | 73 | 45 | 102 |
| 4 | 30 | 7 | 79 | 53 | 111 |
| 5 | 30 | 7 | 80 | 56 | 108 |
| 6 | 30 | 7 | 81 | 50 | 100 |
| 7 | 30 | 7 | 80 | 58 | 106 |
| 8 | 30 | 7 | 75 | 60 | 111 |
| 9 | 100 | 7 | 84 | 74 | 104 |
| 10 | 100 | 7 | 87 | 80 | 103 |
| 11 | 100 | 7 | 80 | 86 | 103 |
| 12 | 100 | 7 | 78 | 73 | 108 |
| 13 | 100 | 7 | 81 | 77 | 94 |
| Clofibrate | 300 | 7 | 90 | 76 | 144 |

[1]Index = $\frac{\text{Treated value}}{\text{Control value}} \times 100$

[2]Relative liver weight = Liver weight (g)/100 g of body weight

What is claimed is:

1. A bisphenoxy carboxylic acid derivative represented by the general formula,

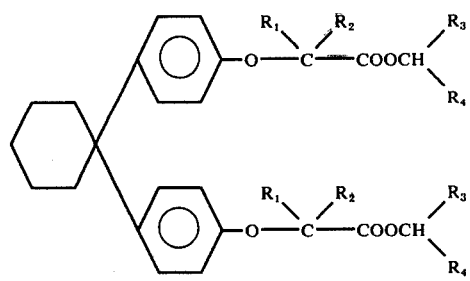

wherein $R_1$ and $R_2$ represent lower alkyl groups, $R_3$ is hydrogen and $R_4$ represents an amino-lower-alkyl group or an N-lower-alkylaminoalkyl group and its acid addition salt.

2. The compound according to claim 1 of the formula,

Synthesis of 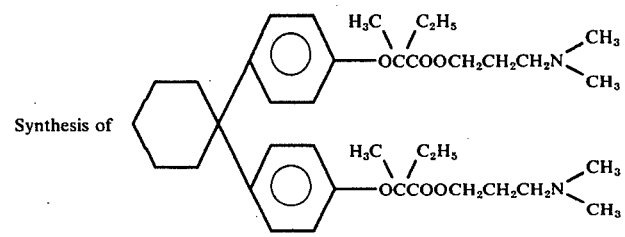

and its acid addition salt.

3. The compound according to claim 1 of the formula,

Synthesis of 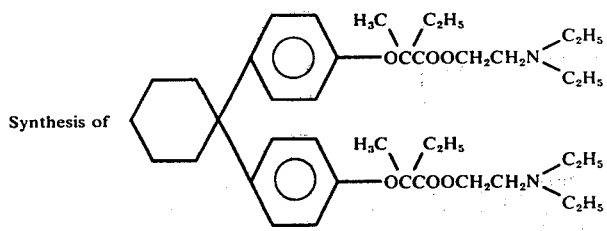
and its acid addition salt.
4. The compound according to claim 1 of the formula,
Synthesis of 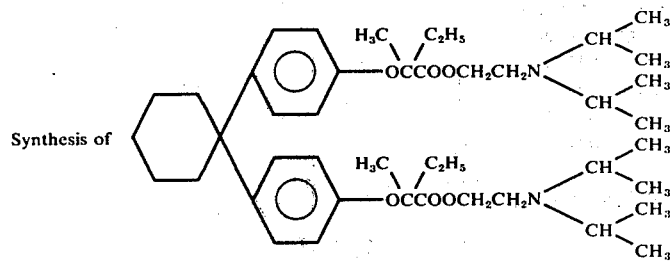
and its acid addition salt.
5. The compound according to claim 1 of the formula,
Synthesis of 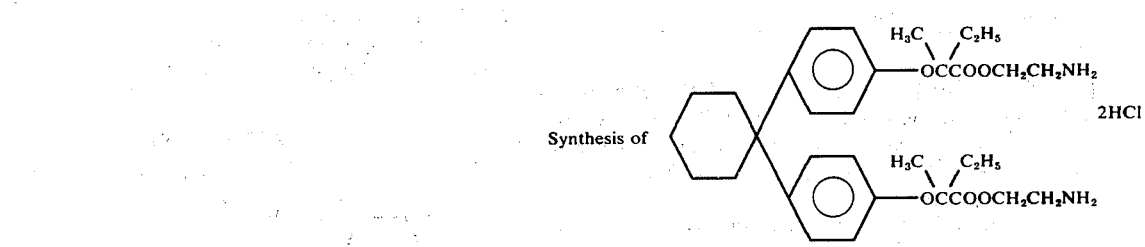
* * * * *

UNITED STATES PATENT AND TRADEMARK OFFICE
CERTIFICATE OF CORRECTION

PATENT NO. : 4,008,265
DATED : February 25, 1977
INVENTOR(S) : Yoshio SUZUKI et al.

It is certified that error appears in the above—identified patent and that said Letters Patent are hereby corrected as shown below:

In the heading of the Patent please insert:

Foreign Application Priority Data

May 22, 1971     Japan ............................. 34866
May 22, 1971     Japan ............................. 34867

Signed and Sealed this

Seventh Day of June 1977

[SEAL]

*Attest:*

RUTH C. MASON
*Attesting Officer*

C. MARSHALL DANN
*Commissioner of Patents and Trademarks*